United States Patent
Slotke et al.

(10) Patent No.: US 6,315,565 B1
(45) Date of Patent: Nov. 13, 2001

(54) METHOD AND APPARATUS FOR TOOTH CLEANING USING ABRASIVE POWDERS

(75) Inventors: Noel Slotke; Richard H. Paschke, both of Timonium, MD (US); Allen G. Hoube, Forest Hills; Robert J. Schuman, New York, both of NY (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/422,422

(22) Filed: Oct. 21, 1999

Related U.S. Application Data

(63) Continuation of application No. 08/720,063, filed on Sep. 27, 1996, now abandoned.

(51) Int. Cl.⁷ ................................................. A61C 15/00
(52) U.S. Cl. .............................. 433/216; 433/116; 433/88
(58) Field of Search .............................. 433/80, 88, 116, 433/215, 216

(56) References Cited

U.S. PATENT DOCUMENTS

| | | | |
|---|---|---|---|
| D. 287,402 | 12/1986 | Orsing | D24/10 |
| 2,643,456 | 6/1953 | Maurer et al. | 433/88 |
| 3,401,690 | 9/1968 | Martin | 128/172.1 |
| 3,882,865 | 5/1975 | Hatzitheodorou | 128/232 |
| 4,340,365 | 7/1982 | Pisanu | 433/80 |
| 4,386,911 | 6/1983 | Maloney et al. | 433/125 |
| 4,412,402 | 11/1983 | Gallant | 51/439 |
| 4,424,036 | 1/1984 | Lokken | 433/116 |
| 4,611,992 | 9/1986 | Lokken | 433/116 |
| 4,850,868 | 7/1989 | Wright et al. | 433/116 |
| 4,884,968 | 12/1989 | Stien | 433/116 |
| 4,906,187 | 3/1990 | Amadera | 433/80 |
| 4,917,603 | 4/1990 | Haack | 433/29 |
| 5,067,899 | 11/1991 | Pascal | 433/80 |
| 5,131,846 | 7/1992 | Hall | 433/116 |
| 5,145,367 | 9/1992 | Kastin | 433/84 |
| 5,197,876 | 3/1993 | Coston | 433/116 |
| 5,338,195 | 8/1994 | Flannagan | 433/116 |
| 5,342,196 | 8/1994 | Van Hale | 433/82 |
| 5,356,292 | 10/1994 | Ho | 433/88 |
| 5,378,150 | 1/1995 | Harrel | 433/91 |
| 5,531,722 | 7/1996 | Van Hale | 604/280 |
| 5,547,376 | 8/1996 | Harrel | 433/116 |
| 5,554,026 | 9/1996 | Val Hale | 433/82 |

FOREIGN PATENT DOCUMENTS

WO 96/12447    5/1996    (WO).

*Primary Examiner*—Nicholas D. Lucchesi
(74) *Attorney, Agent, or Firm*—Dale R. Lovercheck; James B. Bieber

(57) ABSTRACT

A tooth cleaning system having a unitary elastomeric injection molded flexible protective shield, and a nozzle having an end portion extending into the shield. The shield is connected to a source of vacuum and has an inner wall having an inner wall perimeter. The nozzle is connected to a fluid source. The fluid from the fluid source travels directly from the nozzle to less than half of the area enclosed by the perimeter. The nozzle is pivotally supported whereby the nozzle is readily repositioned to positions angularly offset from the central axis of the shield to direct fluid from the nozzle to the entire tooth surface enclosed by the perimeter of the shield. The invention provides a method of cleaning teeth including providing a flexible plastic shield positioned against a tooth surface while pressure within the chamber formed by the flexible protective shield and the tooth surface is reduced to a pressure below ambient atmospheric pressure.

21 Claims, 6 Drawing Sheets

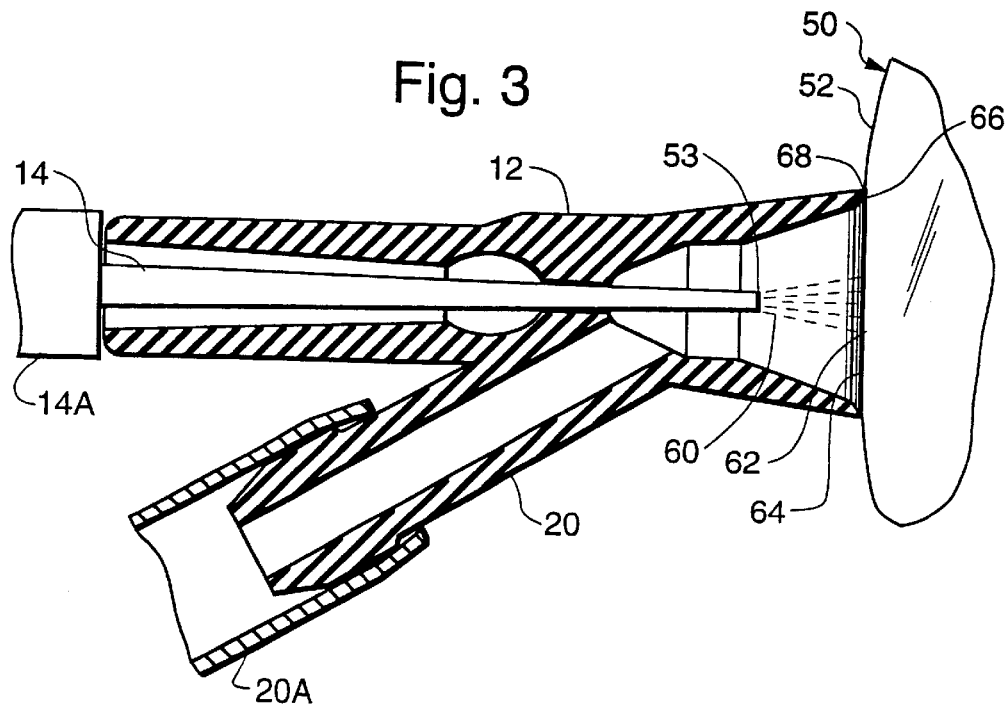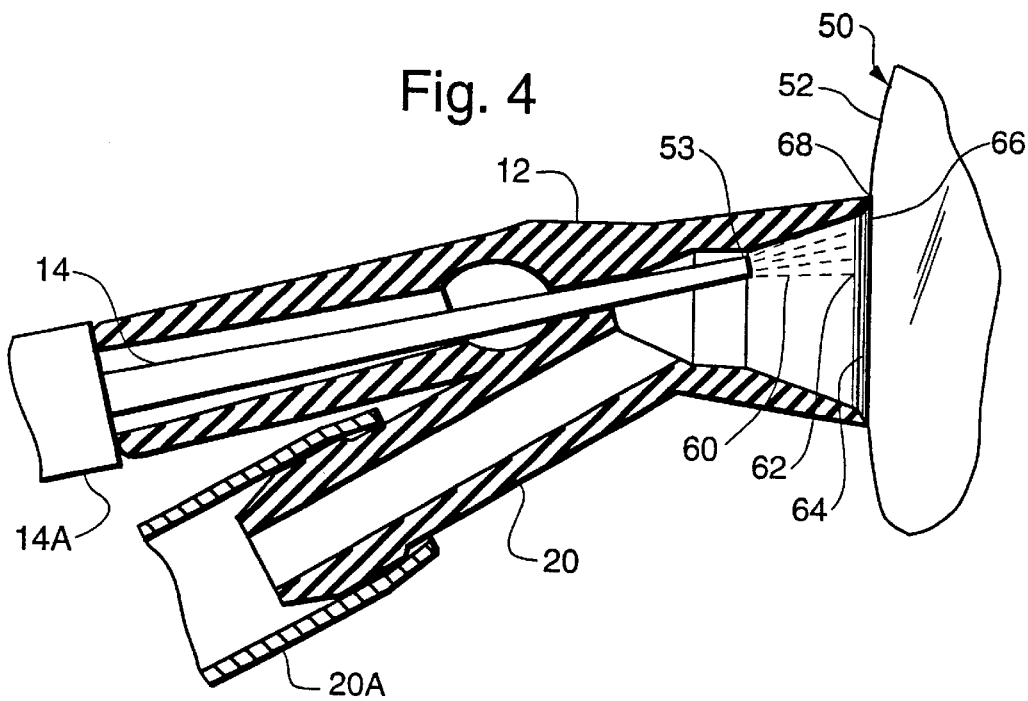

METHOD AND APPARATUS FOR TOOTH CLEANING USING ABRASIVE POWDERS

This application is a con't of Ser. No. 08/720,063 filed Sep. 27, 1996, abandoned.

The invention relates to tooth cleaning method and apparatus using abrasive powders. The invention provides a method and apparatus of tooth cleaning using abrasive powders applied to tooth surface within a flexible guard (or shield). A powder containing spray is readily applied directly to the entire surface area of the tooth enclosed by the guard by angularly displacing the nozzle from the central axis of the guard. The shield forms a vacuum chamber with a tooth outer surface, and the nozzle either pivots within the nozzle channel of the shield or bending the channel to direct spray to all areas of the tooth enclosed by the shield.

The invention enables the nozzle to be oriented at various angles with respect to the tooth surface while the flexible rubber shielding maintains a peripheral engagement with the surface.

During use prior art nozzle shields loose engagement of the shield to the tooth surface at the peripheral edge of the shield. The invention allows the user to move the nozzle by bending the nozzle channel while the shield retains a fluid tight seal with the tooth outer surface.

The invention reduces user strain by reducing the bending of the wrist required to keep shield in engagement with tooth. The clinician preferably swivels or rotates the nozzle using a fulcrum. The user may sit in an ergonomically correct body position and hand position. This aids in preventing hyper-extending the wrist and over-rotating the shoulder to maintain shield adaptation.

Harrel in International application WO 96/12447 discloses a method and apparatus for removing abrasive powders. Harrel in U.S. Pat. No. 5,378,150 discloses methods and apparatus for controlling the aerosol envelope generated by ultrasonic devices. Coster U.S. Pat. No. 5,197,876 discloses a splatter guard for air polishing devices. Wright et al in U.S. Pat. No. 4,850,868 disclosed a spray shield.

The invention overcomes remove the problems of the prior art.

It is the object of the invention to provide a method of cleaning a tooth by providing a tooth cleaning device having a nozzle extending through a protective shield having a flexible conical cleaning chamber wall, a nozzle channel and a suction channel in fluid flow communication with a cleaning chamber enclosed by the cleaning chamber wall. The nozzle channel has a central generally cylindrical wall portion and an outer end portions formed by generally conical walls. Positioning the protective shield against an outer surface of a tooth and drawing vacuum (pressure less than the pressure of the adjacent atmosphere) in the cleaning chamber a seal is formed. By pivotally directing the nozzle so that the central axis of the nozzle forms angles to the central axis of the cylindrical portion of the nozzle channel without substantially bending the shield whereby substantially the entire outer surface of the tooth enclosed by the protective shield is effectively cleaned.

It is an object of the invention to provide a method of cleaning teeth by providing a flexible plastic shield having a nozzle channel therethrough and a rigid nozzle extending through the nozzle channel. The entire area within the shield is cleaned by positioning the flexible protective shield against a tooth surface reducing the pressure within the chamber formed by the flexible protective shield and the tooth surface to a pressure below the pressure of the adjacent atmosphere bending the nozzle channel by pressing the nozzle against opposite sides of the nozzle channel and maintaining a fluid tight seal at the perimeter of the protective shield.

Tooth cleaning as used herein refers to removal of debris from at least one outer surface of a tooth in a patient's mouth by spraying fluidized powder against the surface(s).

BRIEF DESCRIPTION OF THE DRAWINGS

FIG. 3 is a cross-sectional side view of the shield shown in FIGS. 1 and 2 with a nozzle inserted therein aligned with the central axis of the shield.

FIG. 4 is a cross-sectional side view of the shield shown in FIG. 3 with the nozzle at an angle offset to the central axis of the shield.

BRIEF DESCRIPTION OF THE INVENTION

Figure 1:
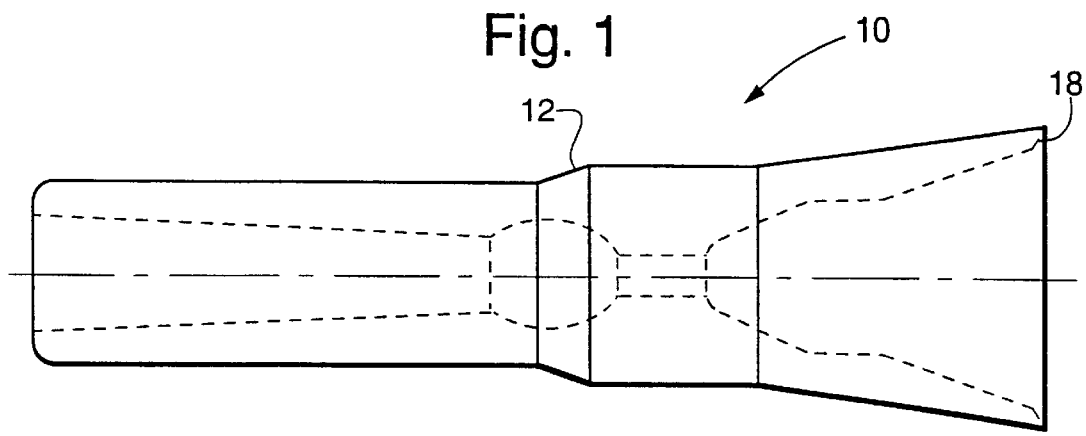
FIG. 1 is a top view of a nozzle holding protective vacuum shield in accordance with the invention.
Figure 2:
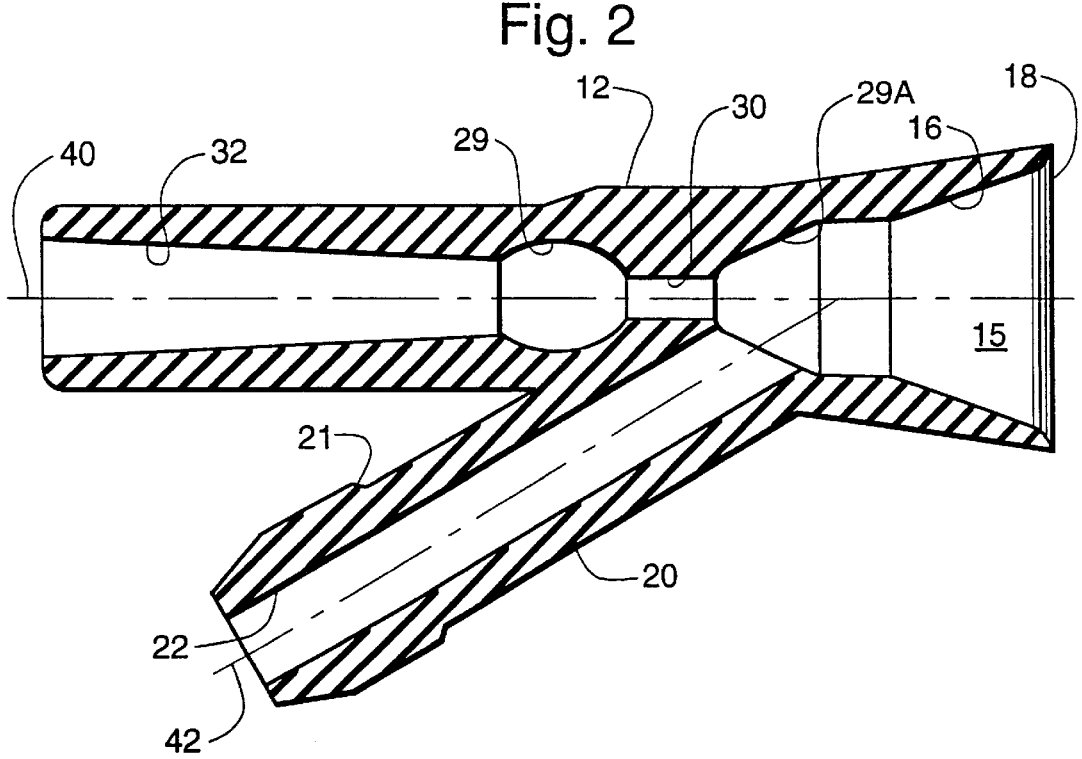
FIG. 2 is a cross-sectional side view of the shield shown in FIG. 1.
Figure 5:
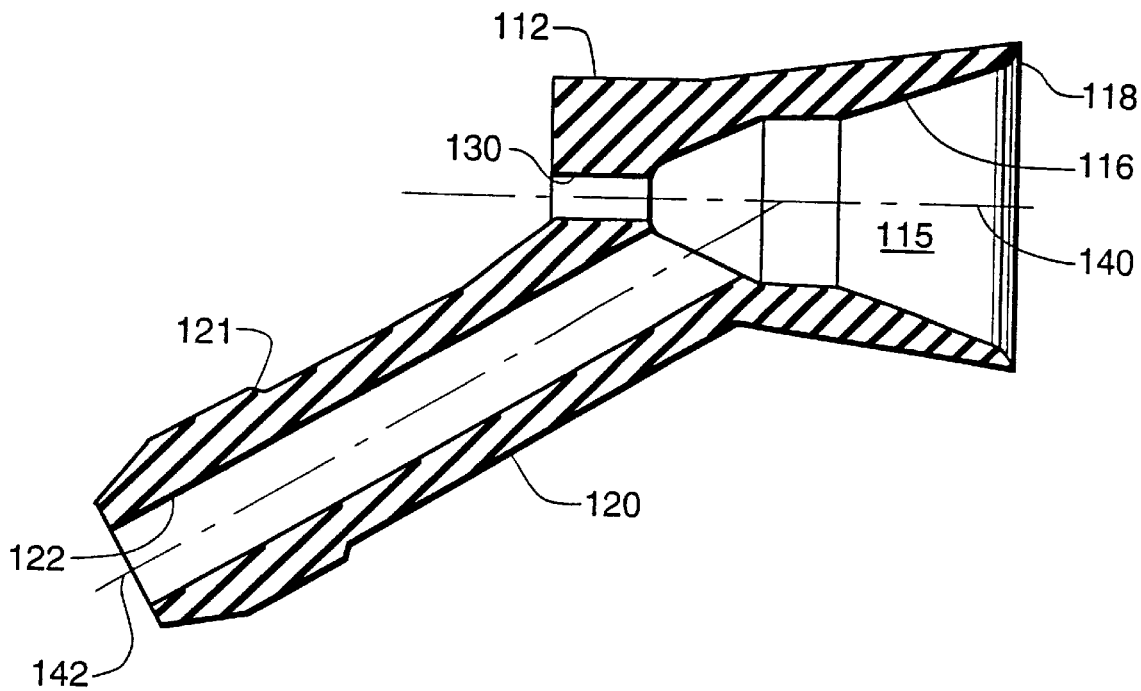
FIG. 5 is a cross-sectional side view of a shield in accordance with a preferred embodiment of the invention.
Figure 6:
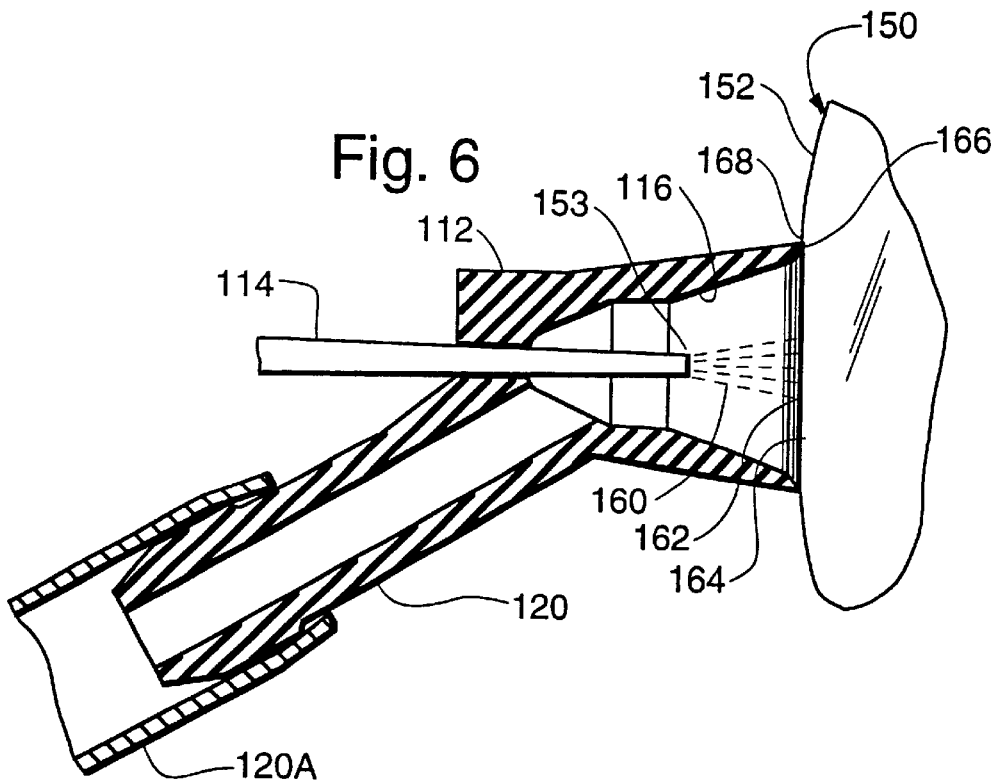
FIG. 6 is a cross-sectional side view of the shield shown in FIG. 5 with a nozzle inserted therein in alignment with the central axis of the shield.

In a tooth cleaning system having a flexible protective shield, and a nozzle having an end portion extending into a cleaning chamber formed by the shield. The shield is connected to a source of vacuum and has an inner wall having an inner wall perimeter. The nozzle is connected to a fluid source. The fluid from the fluid source travels directly from the nozzle to less than half of the area enclosed by the perimeter. The perimeter forms a fluid tight seal with the tooth outer surface. The improvement includes pivotally supporting the nozzle whereby the nozzle is readily repositioned to positions angularly offset from the central axis of the shield directing fluidized powder from the nozzle to the entire tooth surface enclosed by the perimeter.

A preferred embodiment of the invention provides a method of cleaning teeth by providing a flexible plastic shield having a nozzle channel therethrough and a rigid nozzle extending through the nozzle channel. The flexible protective shield is positioned against a tooth surface and the pressure within a cleaning chamber formed by the flexible protective shield and the tooth surface is reduced to a pressure below atmospheric pressure of the air atmosphere of adjacent to the tooth surface outside of the cleaning chamber and shield. Then the entire tooth surface area enclosed by the shield is cleaned by bending the nozzle channel and maintaining a fluid tight seal at the perimeter of the protective shield.

The invention provides a dental tooth cleaning system including a nozzle and a unitary elastomeric injection molded flexible protective shield. The flexible protective shield has a cleaning chamber wall, a cylindrical vacuum conduit wall having an effectively linear vacuum conduit central axis and a cylindrical nozzle channel wall having an effectively linear channel central axis. The cleaning chamber wall encloses a cleaning chamber. The nozzle has a nozzle body and a nozzle orifice end. The nozzle body is integrally connected to the nozzle orifice end. The nozzle orifice end is positioned within the cleaning chamber. The vacuum conduit central axis intersects the nozzle channel central axis at an acute angle. The nozzle has a nozzle axis and an end portion. The nozzle body extends through the nozzle channel into the cleaning chamber. The shield is connected to a source of vacuum. The shield has a cleaning chamber wall having an inner wall having an inner wall perimeter. The perimeter forms a fluid tight seal with a tooth outer surface, the inner wall and the tooth outer surface forms a cleaning chamber. The cleaning chamber wall is integrally connected to the nozzle channel wall. The cleaning chamber wall is integrally connected to the vacuum conduit wall, the nozzle and the nozzle channel is adapted to seal a vacuum in the chamber. The nozzle is connected to a fluid source, and fluid from the fluid source travels directly from the nozzle to less than half of the tooth surface area enclosed by the perimeter. By pivotally supporting the nozzle it is readily repositioned to positions in which the nozzle axis is angularly offset from the central axis of the shield and the fluid directly travels from the nozzle to substantially the entire tooth outer surface area enclosed by the perimeter.

The invention provides a method of cleaning dental teeth, including: providing a flexible plastic shield having a nozzle channel therethrough and a rigid nozzle extending through the nozzle channel. Dental teeth are cleaned by positioning the flexible protective shield against a tooth surface to form a chamber having atmospheric pressure therein, reducing the pressure within the chamber formed by the flexible protective shield and the tooth surface to a pressure below atmospheric pressure, and bending the nozzle channel by pressing the nozzle against opposite sides of the nozzle channel and maintaining a fluid tight seal at the perimeter of the protective shield.

The invention provides a dental tooth cleaning unitary elastomeric rubber injection molded flexible protective shield, the flexible protective shield having a cleaning chamber wall, a vacuum conduit wall having a vacuum conduit central axis and a nozzle channel wall having a nozzle channel central axis, the cleaning chamber wall enclosing a cleaning chamber. The cleaning chamber wall is integrally connected to the nozzle channel wall, the cleaning chamber wall is integrally connected to the vacuum conduit wall. The vacuum conduit central axis intersects the nozzle channel central axis at an acute angle. The nozzle has a nozzle axis and an end portion. The shield has a cleaning chamber wall having an inner wall having an inner wall perimeter, whereby the perimeter forms a fluid tight seal with a tooth outer surface, and the inner wall and the tooth outer surface forms a cleaning chamber. Preferably the nozzle channel wall has a slot wall extending therethrough. Preferably the vacuum conduit wall extends further from the inner wall perimeter of the cleaning chamber wall than the nozzle channel wall extends from the inner wall perimeter of the cleaning chamber wall. Preferably protective shield is used in combination with a nozzle. Preferably the nozzle has a nozzle body and a nozzle orifice end, the nozzle body is integrally connected to the nozzle orifice end, the nozzle orifice end is positioned within the cleaning chamber, the vacuum conduit central axis intersecting the nozzle channel central axis at an acute angle, the nozzle having a nozzle axis and an end portion, the nozzle body extending through the nozzle channel into the cleaning chamber, the shield having a cleaning chamber wall having an inner wall having an inner wall perimeter.

The invention provides a dental tooth cleaning unitary elastomeric molded flexible protective shield, the flexible protective shield having a cleaning chamber wall, and a nozzle channel wall having an effectively linear nozzle channel central axis, the cleaning chamber wall enclosing a cleaning chamber. The cleaning chamber wall is integrally connected to the nozzle channel wall. The shield has a cleaning chamber wall having an inner wall having an inner wall perimeter, whereby the perimeter effectively forms a fluid tight seal with a tooth outer surface, and the inner wall and the tooth outer surface forms a cleaning chamber. Preferably the shield further includes a vacuum conduit wall having a vacuum conduit central axis. Preferably the cleaning chamber wall is integrally connected to the vacuum conduit wall, the vacuum conduit central axis intersecting the nozzle channel central axis at an acute angle, and the nozzle channel wall has a slot wall extending therethrough.

The invention provides a dental tooth cleaning method, including: providing a nozzle and a unitary elastomeric rubber injection molded flexible protective shield, the shield having a cleaning chamber wall having an inner wall having an inner wall perimeter, forming a fluid tight seal between the perimeter and a tooth outer surface, whereby the inner wall and the tooth outer surface forms a cleaning chamber. The cleaning chamber wall is integrally connected to the nozzle channel wall. The cleaning chamber wall is integrally connected to the vacuum conduit wall. The nozzle and the nozzle channel is adapted to seal a vacuum in the chamber. Preferably the method further including connecting the nozzle to a fluid source, and fluid from the fluid source traveling directly from the nozzle to less than half of the tooth surface area enclosed by the perimeter, and pivotally supporting the nozzle whereby the nozzle is readily repositioned to positions in which the nozzle axis is angularly offset from the central axis of the shield and the fluid directly travels from the nozzle to substantially the entire tooth outer surface area enclosed by the perimeter. Preferably the method further includes connecting the shield to a source of vacuum.

DETAILED DESCRIPTION OF THE INVENTION

The invention is now described with more particular reference to FIGS. 1–12. Nozzle holding flexible vacuum shield 12 supports rigid nozzle 14. Shield 12 has a central channel 16. Shield 12 has a cleaning chamber 15 enclosed by inner conical wall 16. Flexible vacuum shield 12 is preferably made of elastomeric rubber by injection molding. Preferably, shield 12 is made of elastomeric material having a durometer shore between A40P/N and A80P/N. More preferably, shield 12 is made of elastomeric rubber having a durometer shore from A42P/N to A67P/N. Most preferably the elastomeric rubber used to make shield 12 has a durometer shore of A67P/N.

Central nozzle channel axis 40 intersects central vacuum channel axis 42 while forces sufficient to bend shield 12 are not being applied to shield 12 by nozzle 14. Generally cylindrical central nozzle channel wall 30 is narrow and adapted to seal a vacuum in the cleaning chamber 15 when nozzle 14 is inserted through the channel enclosed by nozzle channel wall 30. Generally conical portions nozzle channel wall portions 29 and 29A are adapted to allow nozzle positioning flexibility.

Vacuum conduit 20 has flange 21 which is adapted to hold a vacuum seal against a vacuum conduit. Inner wall 22 of the vacuum conduit 20 is in fluid flow communication with the cleaning chamber 15.

With more particular reference to FIG. 3, it is seen that nozzle 14 extends from flange 14A through the nozzle channel into the cleaning chamber. Nozzle orifice 53 is positioned in the cleaning chamber 15. Cleaning spray 60 passes from nozzle orifice 53 through cleaning chamber 15 to the outer surface of 52 of tooth 50. While the nozzle central axis is coaxial with the central axis of the shield, the spray has an outer perimeter 62. The area within the outer perimeter 62 of the spray is less than half of the area 64 within the shield.

Vacuum drawn through conduit 20A hold the perimeter of the shield 68 into a vacuum tight seal against tooth outer wall 52 at the inner wall perimeter 66 of shield 12.

With more particular reference to FIG. 4, it is seen that the nozzle central axis is angularly offset from the central axis of the shield so that the spray from nozzle orifice 53 contacts the tooth surface 52 at the outer perimeter of the inner wall 66. Thus, by moving the nozzle 14, the spray 60 contacts the entire area enclosed by the shield without moving the shield and without breaking the vacuum seal between the outer perimeter of the shield 68 and the tooth surface 52.

With more particular reference to FIGS. 5–9, it is seen that nozzle holding flexible vacuum shield 112 supports rigid nozzle 114. Shield 112 has a central channel 116. Shield 112 has a cleaning chamber 115 enclosed by inner conical wall 116.

Central nozzle channel axis 140 intersects central vacuum channel axis 142 while forces sufficient to bend shield 112 are not being applied to shield 112 by nozzle 114. Nozzle channel wall 130 is narrow and adapted to seal a vacuum in the cleaning chamber 115 when nozzle 114 is inserted through the channel enclosed by nozzle channel wall 130.

Vacuum conduit 120 has flange 121 which is adapted to hold a vacuum seal against a vacuum conduit. Inner wall 122 of the vacuum conduit 120 is in fluid flow communication with the cleaning chamber 115.

Nozzle 114 extends through the channel enclosed by nozzle channel wall 130 into the cleaning chamber 115. Nozzle orifice 153 is positioned in the cleaning chamber 115. Cleaning spray 160 passes from nozzle orifice 153 through cleaning chamber 115 to the outer surface of 152 of tooth 150. While the nozzle central axis is coaxial with the central nozzle channel axis 140 of the shield, the spray 160 has an outer perimeter 162, having an area which is less than half of the area 164 of the outer surface 152 of tooth 150 within inner perimeter 168 of conical wall 116.

Vacuum drawn through conduit 120A holds inner perimeter 168 in a vacuum tight seal against tooth outer wall 152 at inner perimeter 168 of conical wall 116.

Figure 7:
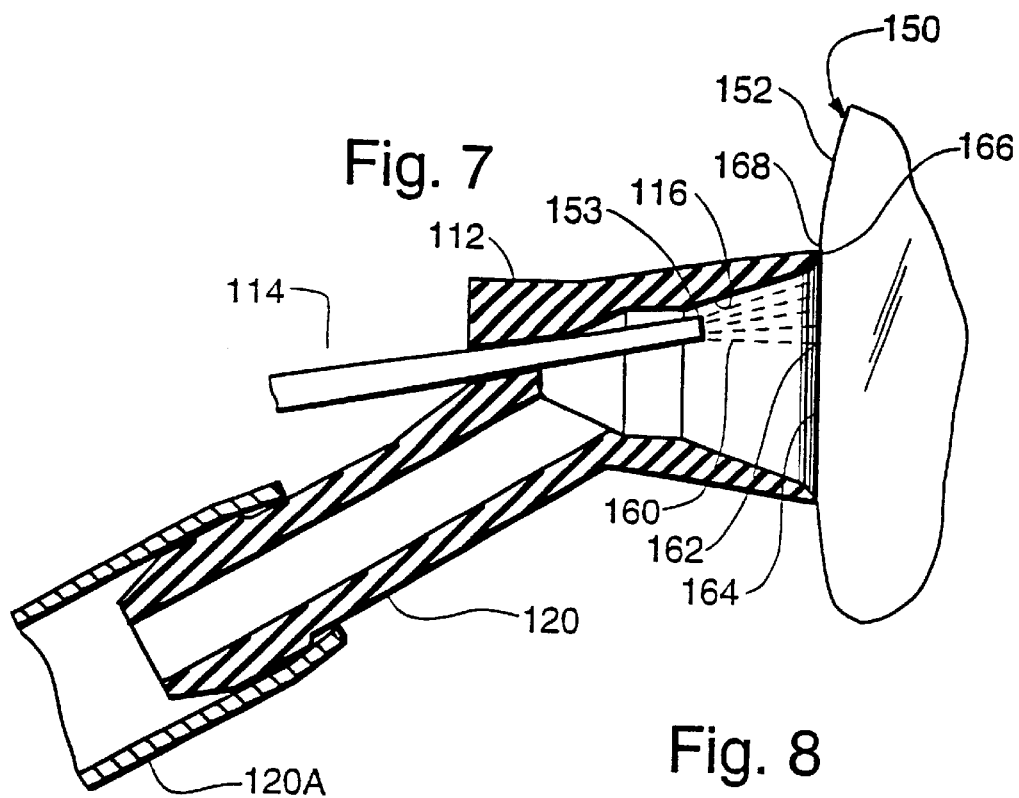
FIG. 7 is a cross-sectional side view of the shield shown in FIG. 6 with a nozzle offset from the central axis of the shield.
Figure 8:
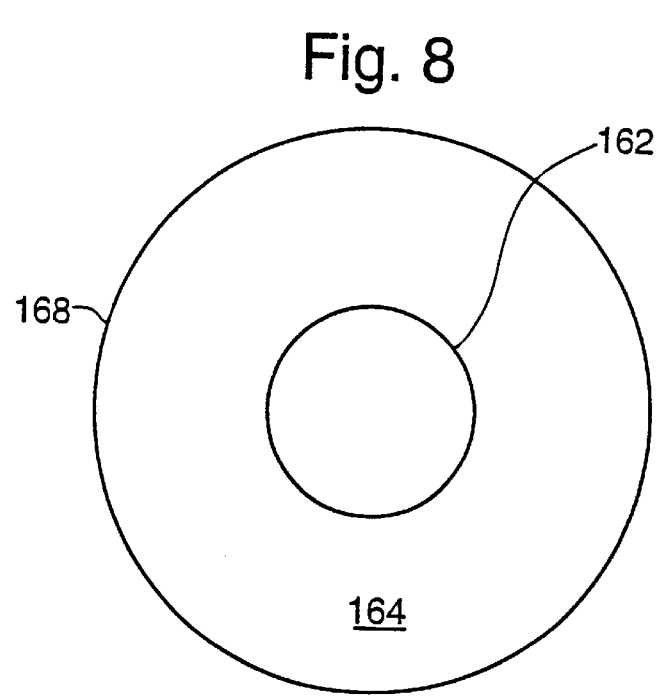
FIG. 8 is a schematic representation of the spray outer perimeter and tooth outer surface within the shield with the nozzle axis coaxial with the nozzle channel axis as shown in FIG. 6.
Figure 9:
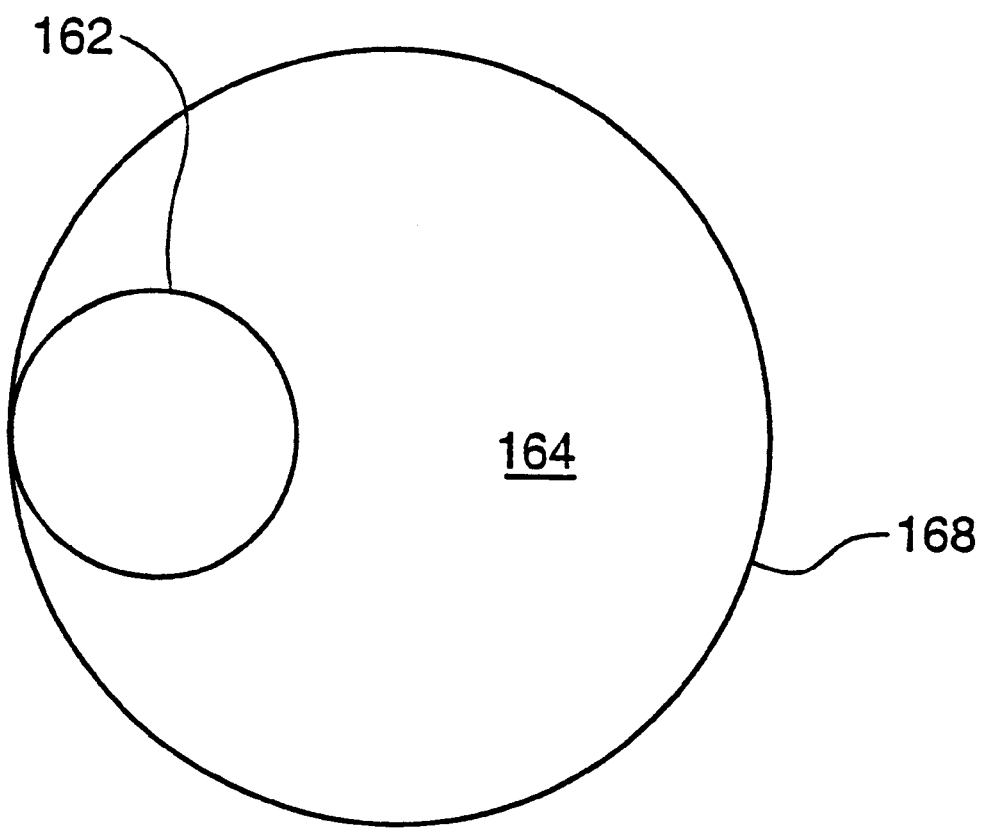
FIG. 9 is a schematic representation of the spray outer perimeter and tooth outer surface within the shield with the nozzle axis offset from the nozzle channel axis as shown in FIG. 7.

With more particular reference to FIGS. 7 and 9, it is seen that the nozzle central axis is angularly offset from the central axis of the shield so that the spray from nozzle orifice 153 contacts the tooth surface 152 at the outer perimeter 168 of conical wall 166. Thus, by moving the nozzle 114 to bend channel wall 130, the spray 160 contacts the entire area enclosed by the inner perimeter 168 without moving inner perimeter 168 on tooth 150 and without breaking the vacuum seal between the inner perimeter 168 and the tooth surface 152.

Figure 10:
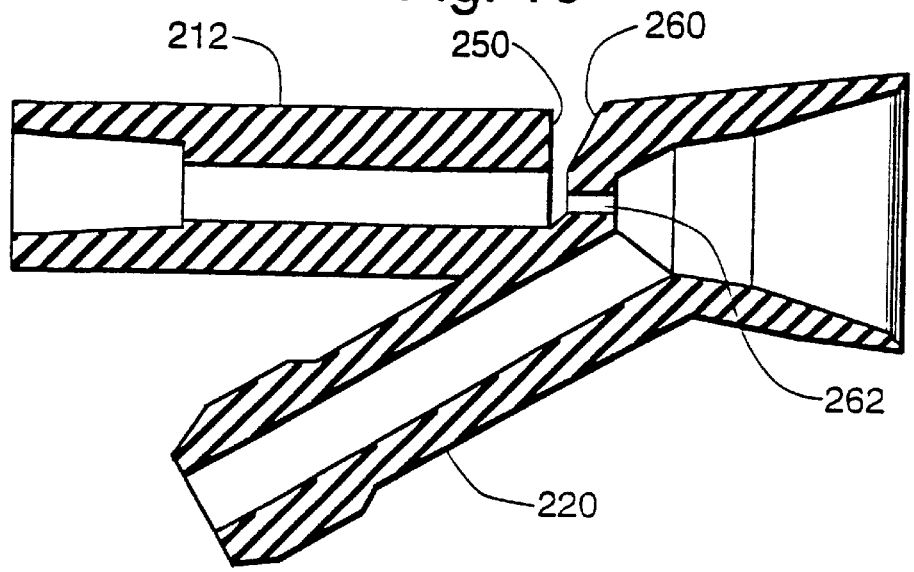
FIG. 10 is a cross-sectional side view of a protective shield in accordance with the invention.
Figure 11:
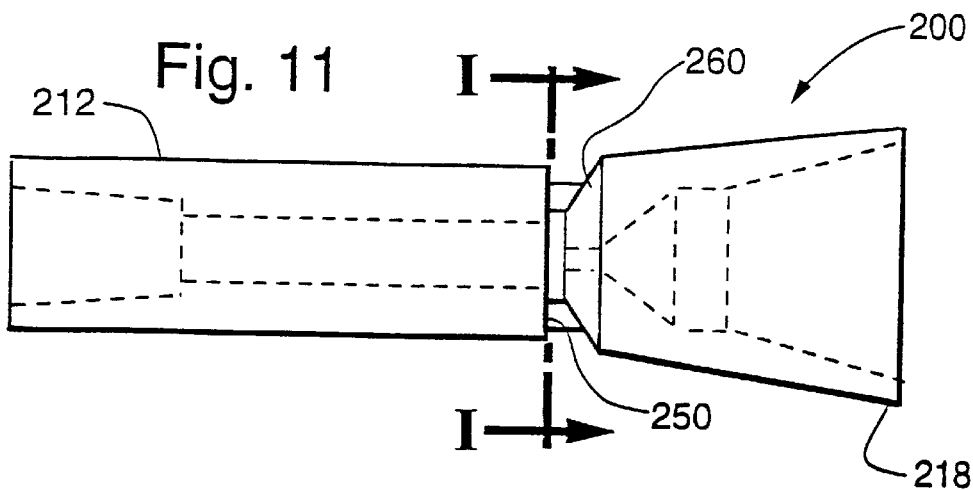
FIG. 11 is a top view of the shield shown in FIG. 10.
Figure 12:
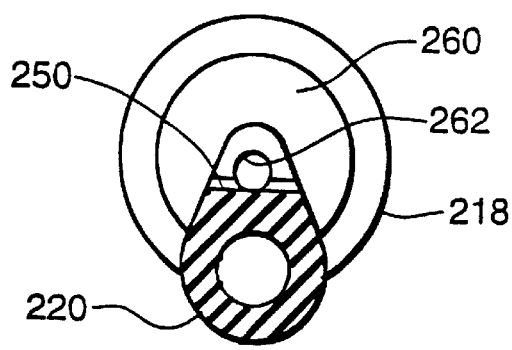
FIG. 12 is a cross-sectional end view along line II in FIG. 11.

With more particular reference to FIGS. 10–12, it is seen that flexible elastomeric shield 200 has a generally cylindrical arm 212, channel wall 262 and generally conical chamber wall 218. Slot wall 250 is perpendicular to the central axis of the channel enclosed by cylindrical channel wall 262. Slot wall 250 intersects the central axis of the channel enclosed by wall 262. Chamfered wall 260 is adjacent to slot wall 250. Slot wall 250 and chamfered wall 260 form a groove across shield 200. Cleaning chamber wall 218 is intersected by vacuum conduit 220. Vacuum applied through vacuum conduit 220 reduces the pressure in the cleaning chamber enclosed by wall 218 during use of shield 200 to clean the surface of a tooth in a patient's mouth.

It will be apparent to those skilled in the art that various modifications and changes may be made in the practice and use of the present invention without departing from the scope thereof as set forth in the following claims.

What is claimed is:

1. A dental tooth cleaning system comprising
   a nozzle and
   a unitary elastomeric injection molded flexible protective shield, said flexible protective shield having
      a cleaning chamber wall having an inner wall having an inner wall perimeter,
      a cylindrical vacuum conduit wall having an effectively linear vacuum conduit central axis and
      a cylindrical nozzle channel wall having an effectively linear channel central axis,
   said nozzle having
      a nozzle body and
      a nozzle orifice end,
   said nozzle body being integrally connected to said nozzle orifice end, said nozzle body extending through said nozzle channel, said nozzle orifice end being positioned within said cleaning chamber,
   said vacuum conduit central axis intersecting said nozzle channel central axis at an acute angle,
   said shield being connected to a source of vacuum, said inner wall perimeter of said cleaning chamber wall forms a fluid tight seal with a tooth outer surface, said inner wall and said tooth outer surface enclose a tooth cleaning chamber,
   said cleaning chamber wall being integrally connected to said nozzle channel wall, said cleaning chamber wall being integrally connected to said vacuum conduit wall,
   said nozzle and said nozzle channel being adapted to seal a vacuum in said cleaning chamber, said nozzle being connected to a fluid source, and fluid from said fluid source traveling directly from said nozzle to less than half of the tooth surface area enclosed by said inner wall perimeter,
   said nozzle being pivotally supported by said nozzle channel, said nozzle being readily repositioned to positions in which the nozzle axis is angularly offset from the central axis of said shield and said fluid directly travels from said nozzle to substantially the entire outer surface area of said tooth enclosed by said tooth cleaning chamber.

2. A method of cleaning dental teeth, comprising: providing a unitary elastomeric injection molded flexible protective shield and a rigid nozzle, said flexible protective shield having a cleaning chamber wall, a cylindrical vacuum conduit wall having an effectively linear vacuum conduit central axis and a cylindrical nozzle channel wall having an effectively linear channel central axis, said cleaning chamber wall being integrally connected to said vacuum conduit wall and to said nozzle channel wall, said nozzle extending through said nozzle channel, positioning said flexible protective shield against a tooth surface to form a chamber having atmospheric pressure therein, said vacuum conduit central axis intersecting said nozzle channel central axis in said chamber, reducing the pressure within the chamber formed by the flexible protective shield and the tooth surface to a pressure below atmospheric pressure, bending said nozzle channel by pressing said nozzle against opposite sides of said nozzle channel and maintaining a fluid tight seal at the perimeter of said protective shield.

3. The method of claim 2 wherein said flexible plastic shield comprises: elastomeric material formed by injection molding.

4. A dental tooth cleaning unitary elastomeric rubber injection molded flexible protective shield, having
a cleaning chamber wall,
a vacuum conduit wall having a vacuum conduit central axis and
a nozzle channel wall having a nozzle channel central axis,
said cleaning chamber wall being integrally connected to said nozzle channel wall, said cleaning chamber wall being integrally connected to said vacuum conduit wall,
said vacuum conduit central axis intersecting said nozzle channel central axis at an acute angle,
said cleaning chamber wall having an inner wall having an inner wall perimeter, whereby said perimeter forms a fluid tight seal with a tooth outer surface, and said inner wall and said tooth outer surface forms a cleaning chamber.

5. The protective shield of claim 4 wherein said nozzle channel wall has a slot wall extending therethrough.

6. The protective shield of claim 4 wherein said vacuum conduit wall extends is nearer to said inner wall perimeter of said cleaning chamber wall than said nozzle channel wall.

7. The protective shield of claim 4 in combination with a nozzle.

8. The protective shield of claim 4 in combination with a nozzle, said nozzle having a nozzle body and a nozzle orifice end, said nozzle body being integrally connected to said nozzle orifice end, said nozzle orifice end being positioned within said cleaning chamber.

9. A method comprising:
providing a dental tooth cleaning unitary elastomeric molded flexible protective shield, comprising:
a flexible cleaning chamber wall,
a vacuum conduit wall with a vacuum conduit central axis, and
a nozzle channel wall having an effectively linear nozzle channel central axis,
said cleaning chamber wall being integrally connected to said nozzle channel wall,
said flexible cleaning chamber wall having an inner wall having an inner wall perimeter,
said cleaning chamber wall being integrally connected to said vacuum conduit wall, said vacuum conduit central axis intersecting said nozzle channel central axis at an acute angle, and said nozzle channel wall having a slot wall extending therethrough, and effectively forming a fluid tight seal between said inner wall perimeter and a tooth outer surface, and said inner wall and said tooth outer surface.

10. A dental tooth cleaning method, comprising:
providing a nozzle and
a unitary elastomeric rubber injection molded flexible protective shield,
said flexible protective shield having
a cleaning chamber wall,
a vacuum conduit wall having a vacuum conduit central axis and
a nozzle channel wall having a nozzle channel central axis,
said nozzle having a nozzle body and a nozzle orifice end, said nozzle body being integrally connected to said nozzle orifice end,
said vacuum conduit central axis intersecting said nozzle channel central axis at an acute angle, said nozzle body extending through said nozzle channel said shield having a cleaning chamber wall having an inner wall having an inner wall perimeter, forming a fluid tight seal between said perimeter and a tooth outer surface, whereby said inner wall and said tooth outer surface forms a cleaning chamber, said cleaning chamber wall being integrally connected to said nozzle channel wall, said cleaning chamber wall being integrally connected to said vacuum conduit wall, said nozzle and said nozzle channel forming a vacuum seal to said chamber.

11. The method of claim 10 further comprising connecting said nozzle to a fluid source, and conveying fluid from said fluid source directly from said nozzle to a spray area, said spray area is less than half of the tooth surface area enclosed by said inner wall perimeter, and pivoting said nozzle whereby said nozzle is readily repositioned to positions in which the nozzle axis is angularly offset from the central axis of said shield and said fluid directly travels from said nozzle to substantially the entire tooth outer surface area enclosed by said perimeter.

12. The method of claim 10 further comprising connecting said vacuum conduit wall to a source of vacuum.

13. A dental tooth cleaning method comprising
providing a dental tooth cleaning system comprising
a substantially cylindrical rigid nozzle having a rigid nozzle body and a nozzle orifice end, said nozzle body being integrally connected to said nozzle orifice end,
a unitary elastomeric injection molded flexible protective shield having a flexible cleaning chamber wall having an inner wall having an inner wall perimeter, and a substantially cylindrical nozzle channel wall,
said cylindrical rigid nozzle being supported by and extending through said cylindrical nozzle channel,
effectively forming a fluid tight seal between said inner wall perimeter and a tooth outer surface, and said inner wall and said tooth outer surface,
conveying cleaning fluid through said cylindrical rigid nozzle onto a tooth in a patient's mouth whereby said tooth is cleaned.

14. A dental tooth cleaning method comprising
providing a dental tooth cleaning system comprising
a substantially cylindrical rigid nozzle
a unitary elastomeric injection molded flexible protective shield having a flexible cleaning chamber wall having an inner wall having an inner wall perimeter, and a substantially cylindrical nozzle channel wall,
said cylindrical rigid nozzle being supported by and extending through said cylindrical nozzle channel,
effectively forming a fluid tight seal between said inner wall perimeter and a tooth outer surface, and said inner wall and said tooth outer surface,
conveying cleaning fluid through said cylindrical rigid nozzle onto a tooth in a patient's mouth whereby said tooth is cleaned,
said nozzle having a metal nozzle body and a nozzle orifice end, said nozzle body being integrally connected to said nozzle orifice end.

15. A dental tooth cleaning method comprising
providing a dental tooth cleaning system comprising
a substantially cylindrical rigid nozzle
a unitary elastomeric injection molded flexible protective shield having a flexible cleaning chamber wall having an inner wall having an inner wall perimeter, and a substantially cylindrical nozzle channel wall,
said cylindrical rigid nozzle being supported by and extending through said cylindrical nozzle channel,
effectively forming a fluid tight seal between said inner wall perimeter and a tooth outer surface, and said inner wall and said tooth outer surface,
conveying cleaning fluid through said cylindrical rigid nozzle onto a tooth in a patient's mouth whereby said tooth is cleaned,
reducing the pressure within a chamber formed by the inner wall of said flexible protective shield and the tooth surface to a pressure below atmospheric pressure.

16. A dental tooth cleaning method comprising
providing a dental tooth cleaning system comprising
a substantially cylindrical rigid nozzle
a unitary elastomeric injection molded flexible protective shield having a flexible cleaning chamber wall having an inner wall having an inner wall perimeter, and a substantially cylindrical nozzle channel wall,
said cylindrical rigid nozzle being supported by and extending through said cylindrical nozzle channel,
effectively forming a fluid tight seal between said inner wall perimeter and a tooth outer surface, and said inner wall and said tooth outer surface,
conveying cleaning fluid through said cylindrical rigid nozzle onto a tooth in a patient's mouth whereby said tooth is cleaned,
said flexible protective shield is a unitary elastomeric rubber injection molded flexible protective shield.

17. The method of claim 16 wherein said nozzle channel wall has a slot wall extending therethrough.

18. The method of claim 16 wherein said vacuum conduit wall extends is nearer to said inner wall perimeter of said cleaning chamber wall than said nozzle channel wall.

19. The method of claim 16 wherein said nozzle has a nozzle body and a nozzle orifice end, said nozzle body being integrally connected to said nozzle orifice end.

20. A dental tooth cleaning method comprising
providing a dental tooth cleaning system comprising
a substantially cylindrical rigid nozzle
a unitary elastomeric injection molded flexible protective shield having a flexible cleaning chamber wall having an inner wall having an inner wall perimeter, and a substantially cylindrical nozzle channel wall,
said cylindrical rigid nozzle being supported by and extending through said cylindrical nozzle channel,
effectively forming a fluid tight seal between said inner wall perimeter and a tooth outer surface, and said inner wall and said tooth outer surface,
conveying cleaning fluid through said cylindrical rigid nozzle onto a tooth in a patient's mouth whereby said tooth is cleaned,
said flexible protective shield further comprises a vacuum conduit wall having a vacuum conduit central axis, and wherein said cleaning chamber wall is integrally connected to said vacuum conduit wall, said vacuum conduit central axis intersecting said nozzle channel central axis at an acute angle, and said nozzle channel wall has a slot wall extending therethrough.

21. A dental tooth cleaning method comprising
providing a dental tooth cleaning system comprising
a substantially cylindrical rigid nozzle
a unitary elastomeric injection molded flexible protective shield having a flexible cleaning chamber wall having an inner wall having an inner wall perimeter, and a substantially cylindrical nozzle channel wall,
said cylindrical rigid nozzle being supported by and extending through said cylindrical nozzle channel,
effectively forming a fluid tight seal between said inner wall perimeter and a tooth outer surface, and said inner wall and said tooth outer surface,
conveying cleaning fluid through said cylindrical rigid nozzle onto a tooth in a patient's mouth whereby said tooth is cleaned,
providing a nozzle and a unitary elastomeric rubber injection molded flexible protective shield, said flexible protective shield having a cleaning chamber wall, a vacuum conduit wall having a vacuum conduit central axis and a nozzle channel wall having a nozzle channel central axis, said cleaning chamber wall enclosing a cleaning chamber, said nozzle having a nozzle body and a nozzle orifice end, said nozzle body being integrally connected to said nozzle orifice end, said nozzle orifice end being positioned within said cleaning chamber, said vacuum conduit central axis intersecting said nozzle channel central axis at an acute angle, said nozzle having a nozzle axis and an end portion, said nozzle body extending through said nozzle channel into said cleaning chamber, said shield having a cleaning chamber wall having an inner wall having an inner wall perimeter,
forming a fluid tight seal between said perimeter and a tooth outer surface, whereby said inner wall and said tooth outer surface forms a cleaning chamber, said cleaning chamber wall being integrally connected to said nozzle channel wall, said cleaning chamber wall being integrally connected to said vacuum conduit wall, said nozzle and said nozzle channel being adapted to seal a vacuum in said chamber.

* * * * *